United States Patent
Tsukerman et al.

(10) Patent No.: US 9,585,624 B2
(45) Date of Patent: Mar. 7, 2017

(54) SYSTEMS AND METHODS FOR FORCED NON-UNIFORM RADIOPHARMACEUTICAL UPTAKE

(71) Applicant: General Electric Company, Schenectady, NY (US)

(72) Inventors: Leonid Tsukerman, Q. Mozkin (IL); Yaron Hefetz, Kibbutz Alonim (IL)

(73) Assignee: GE MEDICAL SYSTEMS ISRAEL, LTD, Brooksfield, WI (US)

( * ) Notice: Subject to any disclaimer, the term of this patent is extended or adjusted under 35 U.S.C. 154(b) by 532 days.

(21) Appl. No.: 14/015,450

(22) Filed: Aug. 30, 2013

(65) Prior Publication Data
US 2015/0065782 A1    Mar. 5, 2015

(51) Int. Cl.
*A61B 5/05*    (2006.01)
*A61B 6/03*    (2006.01)
A61B 6/00    (2006.01)
G06F 19/00    (2011.01)

(52) U.S. Cl.
CPC .............. *A61B 6/037* (2013.01); *A61B 6/032* (2013.01); *A61B 6/503* (2013.01); *A61B 6/5205* (2013.01); *A61B 6/5235* (2013.01); *G06F 19/3406* (2013.01); *A61B 6/501* (2013.01); *A61B 6/502* (2013.01); *G06F 19/321* (2013.01)

(58) Field of Classification Search
CPC ....... A61B 6/037; A61B 6/4057; A61B 6/107; A61B 5/0205; A61B 5/7289
See application file for complete search history.

(56) References Cited

U.S. PATENT DOCUMENTS

| 8,165,663 | B2* | 4/2012 | Hyde | A61B 5/0071 600/476 |
| 2005/0090732 | A1* | 4/2005 | Ivkov | A61N 1/406 600/411 |
| 2010/0056928 | A1* | 3/2010 | Zuzak | A61B 5/0071 600/476 |
| 2011/0178359 | A1* | 7/2011 | Hirschman | A61B 6/037 600/4 |

* cited by examiner

Primary Examiner — Joel Lamprecht
(74) Attorney, Agent, or Firm — Dean D. Small; The Small Patent Law Group, LLC.

(57) ABSTRACT

A method is provided including identifying a target portion of a patient corresponding to a portion of interest of the patient to be scanned with a nuclear medicine scanning technique. The method also includes applying an uptake increasing technique to at least one of the target portion or an application portion of the patient other than the target portion. The uptake increasing technique is configured to increase uptake of a radiopharmaceutical to the target portion of the patient relative to portions of the patient other than the target portion. Also, the method includes administering the radiopharmaceutical to the patient temporally proximate to the applying an uptake increasing technique.

20 Claims, 5 Drawing Sheets

SYSTEMS AND METHODS FOR FORCED NON-UNIFORM RADIOPHARMACEUTICAL UPTAKE

BACKGROUND OF THE INVENTION

The subject matter disclosed herein relates generally to nuclear medicine (NM) imaging systems and techniques, such as single-photon emission computed tomography (SPECT) or positron emission tomography (PET).

NM imaging is generally based on measurement of radiopharmaceutical distribution in a patient's body. A radiopharmaceutical, for example, may be injected into the blood vessels of a patient and be physiologically distributed via blood flow in the entire body of the patient. Generally, the radiopharmaceutical uptake in imaged organs is time limited, and the complete uptake from circulated blood may take from a few seconds to several hours, depending on the pharmaceutical used.

The image quality of the imaged organs is directly proportional to the absolute radio-activity uptake value (or volume concentration) in the imaged organ or tissue. The higher the absolute radio-activity uptake, the better the image quality of the imaged organ or tissue. Image quality may also increased by longer imaging time. However, prolonging the imaging time may cause patient discomfort and reduce throughput of the imaging facility, as well as increase risk of blurring due to patient motion. The absolute radio-activity uptake in imaged organs or tissue is conventionally controlled by injection dose (in terms of absolute volume and/or radio-activity concentration) for the given radiopharmaceutical used. The injection dose of radio-activity is distributed inside the patient body and causes radiation exposure to the patient's organs and tissue until the radiopharmaceutical is reduced to negligible activity, for example, due to physical causes (e.g., half-life or deterioration of the radionuclide) and physiological causes (e.g., wash-out via excretion from the patient body). Generally, the higher the injection dose of radio-activity, the higher the total effective radiation dose of the imaged patient. However, because the radiation dose is administered or distributed to the entire patient body and because only a portion of the patient is imaged, the patient is subjected to higher radiation doses than would otherwise be necessary if radiation were limited to the organ(s) or tissue to be imaged.

BRIEF DESCRIPTION OF THE INVENTION

In accordance with various embodiments, a method for causing non-uniform radiopharmaceutical uptake is provided. The method includes identifying a target portion of a patient corresponding to a portion of interest of the patient to be scanned with a nuclear scanning technique. The method also includes applying an uptake increasing technique to at least one of the target portion or an application portion of the patient other than the target portion. The uptake increasing technique is configured to increase uptake of a radiopharmaceutical to the target portion of the patient relative to portions of the patient other than the target portion. Also, the method includes administering the radiopharmaceutical to the patient temporally proximate to the applying an uptake increasing technique. It may be noted that an uptake increasing technique configured to increase uptake in a target portion may include one or more techniques configured to directly increase uptake in the target portion, and/or one or more techniques configured to indirectly increase uptake in the target portion by decreasing uptake in one or more portions other than the target portion.

In accordance with various embodiments, a system is provided that includes a determination module and an application control module. The determination module is configured to identify a target portion of a patient corresponding to a portion of interest of the patient to be scanned with a nuclear scanning technique. The application control module is configured to, based on an identification of the target portion by the determination module, control application of an uptake increasing technique. The uptake increasing technique is configured to increase uptake of a radiopharmaceutical to the target portion of the patient relative to portions of the patient other than the target portion. The application control module is configured to control application of the uptake increasing technique temporally proximate to an administration of the radiopharmaceutical to the patient.

In accordance with various embodiments, a tangible and non-transitory computer readable medium is provided. The computer readable medium includes one or more computer software modules configured to direct one or more processors to identify a target portion of a patient corresponding to a portion of interest of the patient to be scanned with a nuclear scanning technique. The one or more computer software modules are also configured to direct one or more processors to control application of an uptake increasing technique to at least one of the target portion or an application portion of the patient other than the target portion. The uptake increasing technique is configured to increase uptake of a radiopharmaceutical to the target portion of the patient relative to portions of the patient other than the target portion. The uptake increasing technique is applied temporally proximate to an administration of the radiopharmaceutical to the patient.

DETAILED DESCRIPTION OF THE INVENTION

Figure 1:
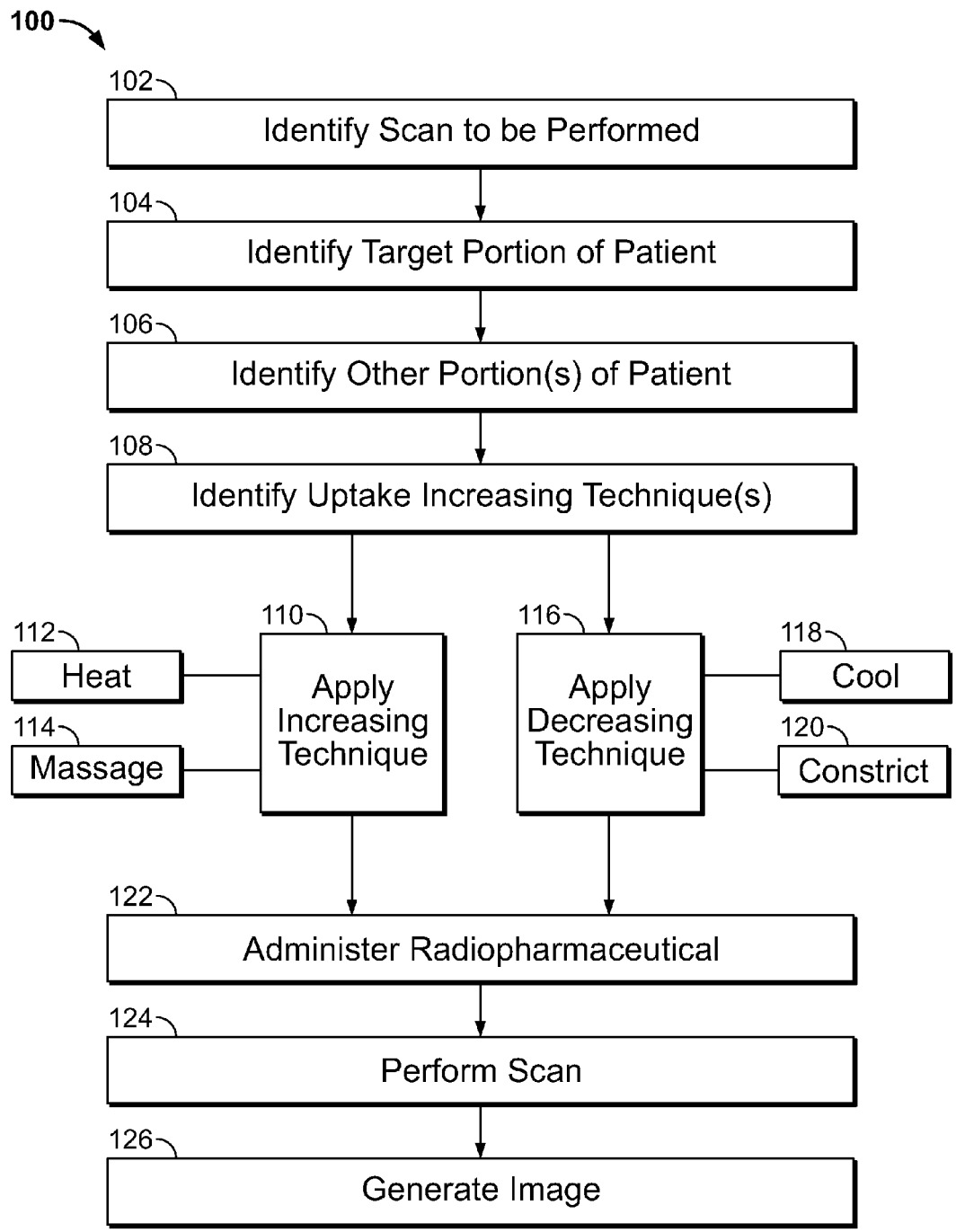
FIG. 1 is a flowchart of a method for causing non-uniform radiopharmaceutical uptake in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. The modules or units shown in the attached figures may represent the hardware that operates based on software or hardwired instructions, the software that directs hardware to perform the operations, or a combination thereof.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "image" or similar terminology is not intended to exclude embodiments in which data representing an image is generated, but a viewable image is not. Therefore, as used herein the term "image" broadly refers to both viewable images and data representing a viewable image. However, certain embodiments generate, or are configured to generate, at least one viewable image.

Various embodiments provide systems and methods for providing non-uniform radiopharmaceutical uptake. For example, in various embodiments, blood flow to a portion of the body corresponding to an image to be acquired may be increased relative to blood flow to other parts of the body at or near the time of administration of a radiopharmaceutical. Various embodiments may reduce overall effective radiation dose administered (by reducing the amount of radiation to non-imaged portions) and/or improve image quality (by increasing the amount of radiation to imaged portions).

In various embodiments, increased radiopharmaceutical uptake in imaged organs and/or decreased radiopharmaceutical uptake in non-imaged organs (or portions of the body not imaged) is provided by forced non-uniform radiopharmaceutical distribution. For example, in some embodiments related to molecular breast imaging (MBI), radiopharmaceutical uptake to breast tissue to be imaged may be increased while uptake to other portions of the body may be decreased. In some embodiments, increased uptake may be achieved by increasing blood flow (relative to other parts of the body) to a target portion of the body to be imaged during administration of a radiopharmaceutical, and/or decreased uptake to other parts of the body may be achieved by reducing blood flow (relative to the target portion of the body). Thus, by increasing blood flow to a target portion relative to other portions of the body, increased amounts of radiopharmaceutical may be delivered via the bloodstream to the target portion, resulting in a more efficient distribution of blood flow and delivered radiopharmaceutical (e.g., more radiopharmaceutical delivered to the target portion and less radiopharmaceutical delivered to other portions). Thus, in some embodiments, by increasing radiopharmaceutical uptake in a portion of the body to be imaged relative to other portions of the body, a reduction in total effective dose may be achieved while still delivering a comparable amount of radiopharmaceutical uptake to the portion of the body to be imaged, thereby maintaining comparable image quality. As another example, if the total effective dose is maintained, an increased amount of radiopharmaceutical may be delivered to the portion of the body to be imaged (relative to the amount delivered with the same dosage but conventional, uniform radiopharmaceutical distribution), resulting in improved image quality and/or allowing the use of less expensive equipment (e.g., less sensitive detectors).

Increased radiopharmaceutical uptake in a portion of the body to be imaged relative to other portions of the body may be achieved, for example, by one or more of the following techniques for preferentially increasing blood flow to the portion of the body to be imaged. For example, the portion of the body to be imaged may be heated, and/or other portions of the body (not to be imaged) may be cooled. As another example, mechanical stimulation of a portion of the body to be imaged may be performed. The mechanical stimulation may include massaging a target organ or body portion manually and/or with a machine. As one more example, pharmaceutical techniques may be employed to increase uptake in a portion of the body to be imaged. Pharmaceutical techniques may include, for example, use of specific hormones that increase blood flow to a particular portion of the body relative to other portions of the body. As yet one more example, hydraulic techniques may be employed. Hydraulic techniques in various embodiments may include the use of one or more tourniquets and/or pressure sleeves over portions of the body, such as limbs, that are not to be imaged. Supplemental techniques may be applied in addition to the above techniques. For example, in some embodiments, supplemental techniques include relaxation (to decrease blood flow to the muscles) and/or fasting (to decrease blood flow to the digestive tract).

Improved targeting or efficiency of radiopharmaceutical uptake distribution is achieved in various embodiments by causing non-uniform radiopharmaceutical distribution in a patient body at or near the time of administration of a radiopharmaceutical to relatively increase radiopharmaceutical uptake in a portion of the body to be imaged and to decrease uptake in other portions of the body not to be imaged. The increase in uptake may be achieved via a physiologic process such as vasodilation, or widening of the blood vessels. Vasodilation may be caused, for example, by external heating of the portion of the body to be imaged. Vasodilation may also be caused, for example, by pharmacological treatment, internally and/or externally. For example, some pharmaceuticals, such as oxytocin, may cause increased blood flow to the breast, and may be used in conjunction with breast imaging.

A decrease in uptake (e.g., by a portion of the body not to be imaged) may be achieved via a physiologic process such as vasoconstriction, or narrowing of the blood vessels. Vasoconstriction may be caused, for example, by cooling a portion of the body. Vasoconstriction may also be caused, by pharmacological treatment, internally and/or externally. Further, vasoconstriction may be caused additionally or alternatively, via a tourniquet or other pressure device. For example, vasoconstriction may be achieved via a blood control suit, such as a pilot flying suit, military anti-shock trousers (MAST), or a pneumatic anti-shock garment (PASG), among others.

In various embodiments, one or more techniques to control the blood flow (e.g., increasing relative blood flow to a portion to be imaged and/or decreasing relative blood flow to one or more portions not to be imaged) may be initially implemented prior to the administration (e.g., injection) of radiopharmaceutical. For example, the blood flow may be controlled for a predetermined amount of time before administration of the radiopharmaceutical corresponding to an amount of time for effective increase (or decrease) of blood flow. As another example, the blood flow control may be implemented until one or more parameters reaches a desired or threshold level (e.g., an elevated temperature of a portion to be imaged, a predetermined reduced temperature of a portion not to be imaged, a measured blood flow difference between a portion to be imaged and one or more portions not to be imaged, or the like), at which time the radiopharmaceutical may be administered. Further, the blood flow control technique(s) may continue to be applied during administration of the radiopharmaceutical. For example, the blood flow control technique(s) may be continually applied after injection of the radiopharmaceutical for a predetermined amount of time corresponding to the amount of time it takes for sufficient blood flow through the body for uptake of substantially all of the radiopharmaceutical. In some embodiments, the predetermined amount of time after the administration of the radiopharmaceutical may be, for example, about 100 seconds.

A technical effect of at least some embodiments is improved image quality. A technical effect of at least some embodiments is reduction of radiation dose and reduced exposure to radiation by patients and hospital staff. A technical effect of at least some embodiments is reduction in cost of imaging procedures. A technical effect of at least some embodiments includes reduction in cost of imaging equipment (for example, in some embodiments, less sensitive imaging detectors may be employed). A technical effect of at least some embodiments is reduction in cost of imaging procedures. A technical effect of at least some embodiments includes reduction in imaging time. A technical effect of at least some embodiments includes reduction of cost of imaging procedures by increasing the productivity of the imaging facility via reducing imaging time. A technical effect of at least some embodiments includes improving patient comfort by reducing imaging time. A technical effect of at least some embodiments includes improving image quality by reducing blurring associated with patient motion by reducing imaging time.

FIG. 1 provides a flowchart of a method 100 for imaging a patient in accordance with various embodiments. In various embodiments, the method 100, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 100 may be able to be used as one or more algorithms to direct hardware to perform one or more operations described herein.

At 102, a scan to be performed is identified. For example, a portion of the body to be scanned may be identified. The portion may be, in various embodiments, the brain, a breast, the heart, a bone or group of bones, or other body portion, organ, or tissue. The scan may also be identified or described with respect to the duration of the scan, the purpose of the scan (e.g., type of diagnosis for which the scan will be used), required image quality of the scan, equipment used (e.g., sensitivity of detectors), amount of radiopharmaceutical required or desired, an amount or level of non-uniformity in the distribution or uptake of the radiopharmaceutical desired or required, or the like. The information identifying the scan may be used, for example, to determine a type or types of uptake increasing techniques to apply, a portion of the body to which to apply an uptake increasing technique, one or more portions of the body to which to apply an uptake decreasing technique, a duration for which to apply an uptake increasing technique, or the like.

At 104, a target portion of the patient is identified. Generally, the target portion may be understood as the portion of the body that will receive one or more applications of a technique or techniques to increase radiopharmaceutical uptake, for example via increased blood flow, to the portion to be scanned. In various embodiments, the target portion corresponds to a portion of the interest of the patient to be scanned (e.g., via a NM imaging technique such as SPECT or PET). For example, in some embodiments, the target portion may be limited to the portion to be scanned. For instance, a breast may be identified as the portion to be scanned and as the target portion. As another example, the target portion may include one or more aspects of the patient surrounding, adjacent, or proximal to the portion to be scanned. For instance, the brain may be identified as the portion to be scanned, and the head may be identified as the target portion. As another example, the heart may be identified as the portion to be scanned, and the upper torso as the target portion. As one more example, the kidneys may be identified as the portion to be scanned, and the lower torso and/or posterior portion of the lower torso may be identified as the target portion. The target portion in some embodiments may be identified autonomously, for example via a distribution targeting module (see FIG. 2 and related discussion) or other processing device. For example, a distribution targeting module may obtain information regarding a scan to be performed from a scanning system, including an identification of the portion of the body to be scanned, and identify a target portion of the body corresponding to the portion to be scanned.

At 106, one or more other portions of the patient that are not to be scanned are identified. The one or more other portions may be identified to receive an application of one or more techniques to decrease radiopharmaceutical uptake, such as via reduced blood flow to the one or more other portions of the patient that are not to be scanned. Thus, the amount of radiopharmaceutical uptake may be non-uniformly distributed in the body by increasing bloodflow in the portion to be scanned (relative to portions not being scanned) and/or decreasing the uptake to portions not being scanned (relative to a portion being scanned), thereby more efficiently distributing the uptake for improved imaging and/or reduced radiation exposure. For example, if the portion to be scanned is the brain, one or more limbs may be identified as portions other than the portion to be scanned, and blood flow reduced to one or more of the limbs shortly before and/or during administration of a radiopharmaceutical.

At 108, one or more uptake increasing techniques are identified. Generally, in various embodiments, an uptake increasing technique may be understood as a technique configured to increase blood flow through the target portion identified at 104. Uptake increasing techniques thus may include techniques that increase blood flow to the target portion. Uptake increasing techniques may also include techniques that decrease blood flow to one or more portions of the body other than the target portion, thereby increasing the blood flow through the target portion relative to the one or more other portions. The type of technique, such as application of heat, massaging or otherwise physically stimulating the target portion, or administration of a pharmaceutical to increase blood flow to a target portion (e.g., oxytocin may be used to increase blood flow to a breast), among others, may be identified. Some non-pharmaceutical substances may have similar effects. For example alcohol may preferentially dilate blood vessels near the skin. Consumption of water may increase the activity of the kidneys. Other foods or beverages may cause increased activity of organs such as the stomach, the intestine, the liver, the kidneys, or the like. The administration of the radiopharmaceutical may be timed to coincide with the desired effect of the administered pharmaceutical. When the brain is the target organ, specific mental tasks, for example performing calculations, solving problems, playing games, watching a movie or listening to music, may increase blood flow to the brain. Fasting may decrease blood flow to the digestive system. Additionally, in some embodiments, an amount of application of the technique may be identified. For example, the amount of time for which a technique is applied may be identified. As another example, a target parameter corresponding to the application of the technique may be set. For instance, if the technique is identified as application of heat, a temperature to which the target portion is to be heated may be identified. Additionally or alternatively, a safety limit (e.g., temperature limit) may be set or otherwise identified.

At 110, a technique (or techniques) is applied to the target portion to increase blood flow and radiopharmaceutical uptake to the target portion. In some embodiments, the technique may be manually applied. In some embodiments, the technique may be manually applied using instructions, recommendations, or other guidance provided via a display. In some embodiments, the technique may be autonomously applied without human intervention. Examples of techniques applied to a target portion to increase blood flow through the target portion include heat, physical stimulation such as massage, or pharmaceutical techniques, among others. In some embodiments, the technique may be applied only to the portion to be scanned, and in some embodiments, the technique be applied to surrounding tissue as well. In some embodiments, use of information from a sensor may be used in the application of the technique. For example, a sensor may be used to determine if a measured parameter (e.g., temperature, blood flow, or the like) has reached a desired level and/or a safety limit, with the application of the technique reduced or stopped responsive to the information from the sensor. For example, an amount of heat applied may be reduced to maintain a temperature at a desired level. As another example, the application of heat may be removed if the temperature exceeds a predetermined safety level.

At 112, for example, heat may be applied to the target portion. Heat may be applied, for example, via a heating pad that is controlled by a practitioner. In other embodiments, the heating pad may be controlled automatically or autonomously, for example, responsive to a measured temperature value of the target portion. Again, as also discussed above, the target portion may be limited to the portion of the body to be scanned. For example, for a breast scan, heat may be applied to the breast to be scanned, or to a portion of the breast to be scanned. In other embodiments, the target portion may include other aspects or portions of the patient. For example, for a heart scan, the torso or a portion thereof (e.g., upper torso) may be heated.

At 114, for example, the target portion may be massaged. Again, the target portion may be the portion being scanned itself or may include other tissue or aspects of the patient surrounding and/or adjacent to the portion to be scanned. As indicated elsewhere herein, other techniques, such as the administration of a pharmaceutical that increases blood flow to a specific portion of the body, may be applied additionally or alternatively.

At 116, a technique (or techniques) is applied to one or more other portions (e.g., portion(s) identified at 106) of the body other than the target portion to decrease blood flow to the other portion(s) and thereby increase radiopharmaceutical uptake to the target portion. In some embodiments, the technique may be manually applied. In some embodiments, the technique may be manually applied using instructions, recommendations, or other guidance provided via a display. In some embodiments, the technique may be autonomously applied without human intervention. Examples of techniques applied to portions other than the target portion to decrease blood flow through the other portions include cooling or the application of pressure. In various embodiments, use of information from a sensor may be used in the application of the technique. For example, a sensor may be used to determine if a measured parameter (e.g., temperature, blood flow, pressure, or the like) has reached a desired level and/or a safety limit, with the application of the technique reduced or stopped responsive to the information from the sensor. For example, an amount of pressure applied may be reduced to maintain a pressure at a desired level. As another example, the application of pressure may be removed if the pressure exceeds a predetermined safety level, or if the pressure has been applied for an amount of time longer than a safety limit. Thus, while blood flow may be reduced to one or more other portions, the blood flow may still be maintained within desired ranges.

At 118, for example, one or more portions of the body other than the target portion may be cooled. In some embodiments, for example, an ice pack may be applied to one or more portions of the body other than the target portion. For example, if a portion of the body near the torso is to be scanned, one or more limbs may be cooled.

At 120, for example, pressure may be applied to reduce blood flow to one or more portions other than the portion to be scanned. For example, a tourniquet, pressure sleeve, pilot flying suit, MAST (Military Anti-Shock Trousers), PASG (Pneumatic Anti-Shock Garments), or the like may be utilized to apply pressure to one or more limbs. The application of pressure may be controlled (e.g., using a measured value of pressure and/or blood flow) to maintain limitations on blood flow within a safety limit, for example, based on amount of pressure and/or amount of time at a given pressure.

At 122, a radiopharmaceutical is administered. In some embodiments, the radiopharmaceutical may be administered (e.g., injected) manually. In some embodiments, the radiopharmaceutical may be applied manually under the control of a processing unit such as an application control module (see FIG. 2 and related discussion), for example via instruction or other guidance provided via a display. In some embodiments, the radiopharmaceutical may be administered autonomously, for example, by an application control module acting to control a pump or other device for administering the radiopharmaceutical intravenously to a patient to be scanned.

Generally, the radiopharmaceutical is applied at a time for which the blood flow to the target portion is increased relative to other portions of the body (by directly increasing blood flow to the target portion and/or by reducing blood flow to other portions). For example, one or more uptake increasing techniques may be applied for a predetermined period of time before administration of the radiopharmaceutical, and/or until a desired parameter value (e.g., temperature of the target portion) is achieved. The radiopharmaceutical may then be administered automatically, as one example, or by a practitioner responsive to an alert or notification, as another example.

Further, the application of one or more uptake increasing techniques may be continued after administration of the radiopharmaceutical. For example, the application of the uptake increasing technique may continue for a predetermined amount of time corresponding to the amount of time taken by blood containing injected radiopharmaceutical to pass through the body. In some embodiments, the predetermined time during which one or more uptake increasing techniques continues may be about 100 seconds.

The administration of the radiopharmaceutical and the application of one or more uptake increasing techniques may be performed temporally proximate to one another. As used herein, application of an uptake increasing technique "temporally proximate" to an administration of radiopharmaceutical may be understood as at or near the time of administration, including, for example, shortly before administration, continued at time of initial administration, and/or continued for a predetermined time after administration (e.g., about 100 seconds for blood to flow through body and for body to uptake radiopharmaceutical). The application of the uptake increasing technique(s) may occur during the same patient visit to a scanning facility for performance of an imaging scan. For example, application of the uptake increasing technique and radiopharmaceutical administration may occur, for example, less than an hour before a scan, less than two hours before a scan, or less than three hours before a scan, in various embodiments. In some embodiments, a practitioner may apply an uptake increasing technique for a given time after administration, while in other embodiments, a practitioner may provide an input such as pressing a button to inform an application control module of the time of radiopharmaceutical administration, and the application control module may control application of the uptake increasing technique for a predetermined amount of time after receiving the notification.

At 124, a scan is performed. The scan, for example, may include acquiring imaging data via one or more imaging techniques, such as NM imaging techniques (e.g., PET, SPECT). Emissions and/or annihilation events corresponding to the administered radiopharmaceutical may be detected as part of performing the scan. At 126, the acquired imaging data may be used to generate an image.

Thus, in various embodiments, because the proportion of radiopharmaceutical delivered to or uptaken by the target portion is higher relative to other parts of body than would have otherwise occurred without the application of the uptake increasing technique(s) temporally proximate to the administration of the radiopharmaceutical (e.g., due to relatively increased blood flow to the target portion during uptake of the radiopharmaceutical), improved image quality relative to overall dose may be achieved. Additionally or alternatively, overall dose may be lowered. Further, in some embodiments, increasing the effectiveness of the radiopharmaceutical uptake (e.g., increasing the uptake by the target portion relative to other portions of the body) may allow the use of less expensive equipment (e.g., less sensitive detectors and/or less intensive processing requirements for image reconstruction).

Figure 2:
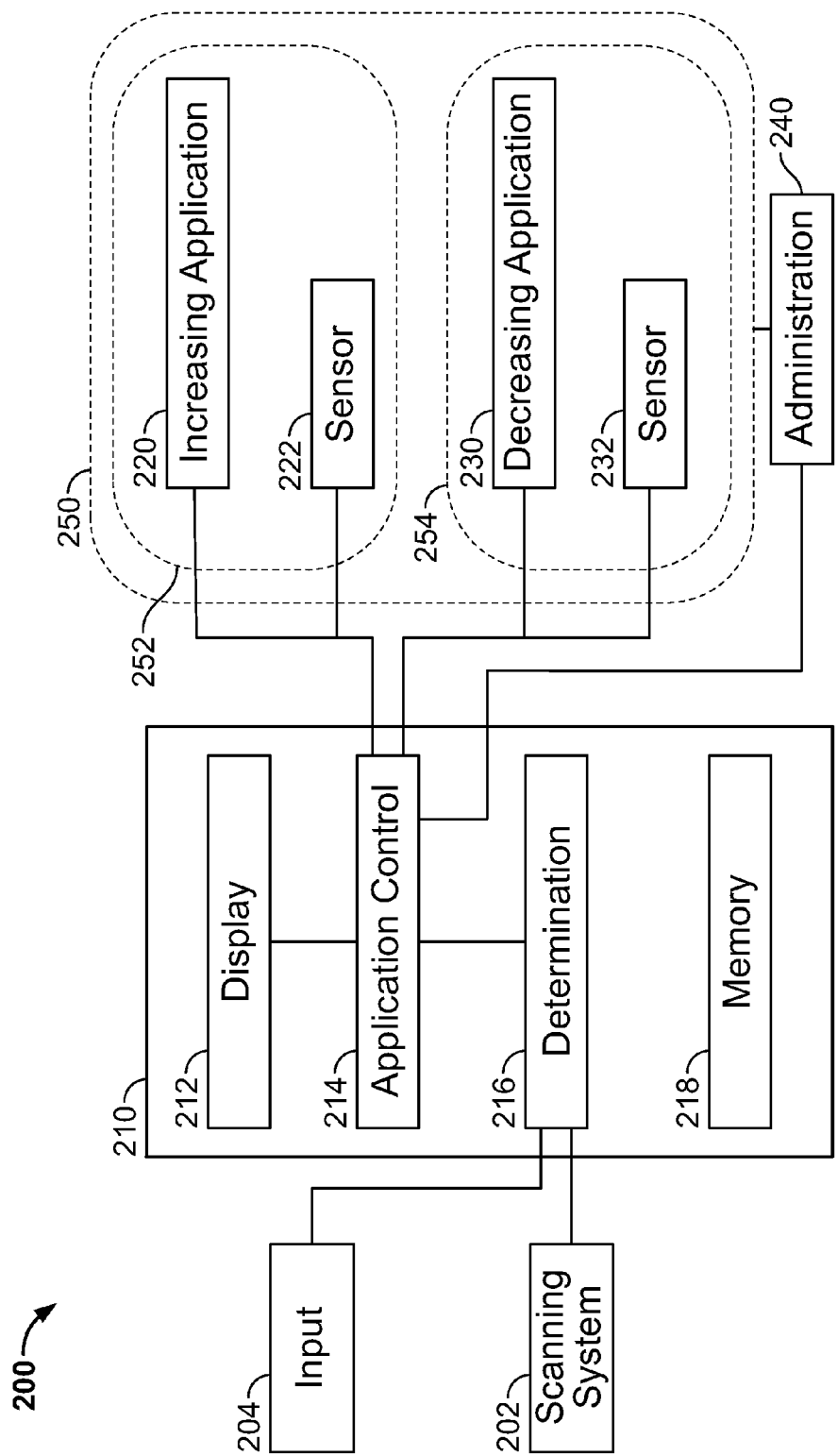
FIG. 2 is a schematic view of a system in accordance with various embodiments.

FIG. 2 provides a schematic view of a system 200 in accordance with various embodiments. In the illustrated embodiment, the system includes a scanning system 202, an input module 204, a distribution targeting module 210, an uptake increasing application device 220, a sensor 222, an uptake decreasing application device 230, a sensor 232, and a radiopharmaceutical administration module 240.

Generally, in the illustrated embodiment, the distribution targeting module 210 receives information regarding a scan to be performed (e.g., by the scanning system 202) from the scanning system 202 and/or the input module 204. The distribution targeting module 210 then determines a target portion corresponding to a portion of the body to be imaged. The distribution targeting module 210 also determines one or more uptake increasing techniques to be applied. The uptake increasing techniques are configured to increase blood flow to the target portion relative to other portions of the body. For example, the uptake increasing application device 220 may apply a technique to the target portion to increase blood flow to the target portion. As another example, the uptake decreasing application device 230 may apply a technique to a portion of the body other than the target portion to decrease blood flow to the portion of the body other than the target portion. The administration module 240 is configured to administer (e.g., inject) a radiopharmaceutical into the patient to be scanned. One or more aspects of the system 200 may be manually controlled by a practitioner; manually operated or performed by a practitioner using instruction, guidance, or other control from the distribution targeting module 210; or be operated or controlled autonomously by the distribution targeting module 210.

In the illustrated embodiment, the scanning system 202 is configured to perform a scan and acquire imaging information from which an image may be reconstructed. The scanning system 202 may be configured to acquire imaging information using NM imaging, such as PET or SPECT. (For an example of a PET system, see FIG. 3 and related discussion. For an example of a SPECT system, see FIG. 4 and related discussion.) The scanning system 202 may also provide information regarding the scan to be performed to the targeting distribution module 210. For example, the scanning system 202 may identify a portion of the body to be scanned (e.g., brain, breast, heart, or kidney, among others) to the targeting distribution module 210. In various embodiments, information regarding the purpose of the scan (e.g., type of diagnosis for which the scan will be used), required image quality of the scan, equipment used (e.g., sensitivity of detectors), amount of radiopharmaceutical required or desired, an amount or level of non-uniformity in the distribution or uptake of the radiopharmaceutical desired or required, or the like may be provided to the targeting distribution module 210, which may in turn use the information to identify a target portion of the body as well as one or more uptake increasing techniques to apply, and, in some embodiments, a duration of time or other level or amount of application of the technique to be employed.

The depicted input module 204 is configured to allow a user to input information (e.g., information regarding a patient and/or a scan to be performed on the patient) for use by the distribution targeting module 210. The input module 204 may include, for example, a keyboard, keypad, mouse, touchscreen, or the like. Information provided via the input module 204 may be employed by the distribution targeting module 210 to identify a target portion for application of an uptake increasing technique and/or a different portion of the body for application of an uptake decreasing technique.

Further, the information may be used to determine a type and/or amount of a technique to be applied. In some embodiments, for example, where a radiopharmaceutical is manually administered, the input module 204 may be configured for use by a practitioner to provide an input notifying the targeting distribution module 210 that the radiopharmaceutical has been administered. Responsive to the receipt of the input indicating that the radiopharmaceutical has been administered, the targeting distribution module 210 may determine a time to cease application of the uptake increasing technique(s), for example about 100 seconds after administration of the radiopharmaceutical.

Generally, in various embodiments, the distribution targeting module 210 is configured to control the application of one or more techniques to increase radiopharmaceutical uptake to a target portion of a patient body corresponding to a portion to be scanned by a NM imaging technique relative to radiopharmaceutical uptake of one or more other portions of the patient body. In various embodiments, the distribution targeting module 210 (and/or sub-modules of the distribution targeting module 210) may include one or more processors and a memory, such as the depicted memory 218. In the illustrated embodiment, the distribution targeting module includes a display module 212, an application control module 214, and a determination module 216. The illustrated arrangement is provided by way of example, as other arrangements may be utilized in other embodiments. For example, one or more aspects of the various modules may be shared with other modules, two or more modules may be joined to atm a module, one or more modules may be separated into multiple modules or sub-modules, or additional or alternative modules may be employed.

In the illustrated embodiment, the display module 212 is configured to display information and/or instruction or other guidance to a practitioner. The display module 212, for example, may include a screen. In various embodiments, the display module 212 may be configured to provide an instruction, recommendation, or other guidance to a practitioner. For example, based on a determined type and/or amount of application of an uptake increasing technique, the display module 212 may provide a display instructing a practitioner to apply one or more techniques to one or more body portions at a given amount or level (e.g., "Apply heat to torso"; "Apply pressure sleeve to arm"; "Massage [target portion] for five minutes"; or the like). In some embodiments, the practitioner may acknowledge receipt and/or performance of the technique using the input module 204. In some embodiments, the display module 212 may be configured to display an alarm or instruction to cease application of an uptake increasing technique (e.g., "Temperature of application portion below desired threshold—Remove icepack or cease cooling"). In embodiments where a given technique is desired to be applied for a given amount of time, the display 212 may provide a timer showing time remaining until ceasing application of the technique.

Generally, in various embodiments, the application control module 214 is configured to control application of an uptake increasing technique (or techniques). For example, the application control module 214 may, based on an identification of a target portion by the determination module 216, control application of a technique to increase uptake of a radiopharmaceutical to the target portion relative to other portions of the patient not desired to be scanned. The application control module 214 may be configured to control application of the uptake increasing technique temporally proximate to an administration of the radiopharmaceutical to the patient. For example, the uptake increasing technique may be applied immediately or shortly before administration of the radiopharmaceutical, during administration of the radiopharmaceutical, and/or shortly after administration of the radiopharmaceutical. "Shortly before" and "shortly after" may be understood to include times within about 1 minute, 2 minutes, or 5 minutes in various embodiments. Other time periods may be utilized in various embodiments.

In some embodiments, the application control module 214 may be configured to control application of an uptake increasing technique by instructing or guiding a practitioner, for example via the display module 212. Additionally or alternatively, the application control module 214 may autonomously control application of an uptake increasing technique by an application device (e.g., uptake increasing application device 220 or uptake decreasing application device 230). The application control module 214 may receive information from sensors (e.g., sensors 222, 232) which the application control module 214 uses to control application of a technique. It may be noted that uptake increasing techniques may include techniques that increase uptake (e.g., blood flow) by the target portion and/or techniques that decrease uptake by portions of the body other than the target portion (thereby increasing relative blood flow to or uptake by the target portion).

In various embodiments, one or more sensors may provide information regarding whether a desired value (e.g., temperature, pressure, blood flow, or the like) for a given portion of the body to which a technique is being applied has been reached, and/or whether a safety limit of a parameter has reached a threshold level. For example, once a desired level of a parameter, such as temperature or blood flow for the target portion, has been reached, the application control module 214 may autonomously administer a radiopharmaceutical, or, as another example, the application control module 214 may display a message to a practitioner indicating that a desired value has been reached and/or an instruction to the practitioner to administer the radiopharmaceutical. Further still, the application control module 140 may control application of the uptake increasing technique (s) for a predetermined amount of time after administration of the radiopharmaceutical while the radiopharmaceutical is distributed through the patient body via blood flow.

In the illustrated embodiment, the determination module 216 is configured to identify a target portion of a patient corresponding to a portion of interest of the patient to be scanned with a NM scanning technique. For example, the determination module 216 may acquire information from the scanning system 202 and/or the input module 204 indicating that the brain is the portion of interest to be scanned. The determination module 216 may then identify the head of the patient as the target portion. As another example, the determination module 216 may receive or otherwise acquire information that a breast is to be scanned, and may identify the breast as the target portion. The determination module 216 may also identify one or more portions of the body that are not to be scanned. The target portion may receive an uptake increasing technique (e.g., a technique to increase blood flow to the target portion) while the other portions of the body not to be scanned receive an uptake decreasing technique (e.g., a technique to decrease blood flow to the identified portions of the body other than the target portion). In FIG. 2, a patient body 250 is depicted schematically as having a target portion 252 and an application portion 254 that is a portion of the body other than the target portion 252. For example, for a brain scan, the target portion 252 may be the head of the patient, and the application portion 254 may include one or more limbs. Uptake increasing techniques may be applied to the target portion 252 and/or uptake decreasing techniques may be applied to the application portion 254, thereby increasing the proportion of total radiopharmaceutical administered that is delivered to and uptaken by the target portion 252.

In the illustrated embodiment, the uptake increasing application device 220 is depicted as being attached to or otherwise associated with the target portion 252. For example, the uptake increasing application device 220 may be configured as a heating pad affixed to, resting on, or otherwise positioned to deliver heat to the target portion. The uptake increasing application device 220 alternatively or additionally may include a mechanical massaging device configured to massage the target portion 252. In the illustrated embodiment, the sensor 222 is also positioned proximate the target portion 252 and is configured to measure a parameter (e.g., temperature, blood flow, or the like) of the target portion 252. Based on information provided by the sensor 222, the control of the uptake increasing device 220 may be altered. For example, if the value of the measured parameter meets or exceeds a desired value, the application control module 214 may, responsive to receipt of the information form the sensor 222 indicating that the desired value has been met, autonomously reduce or remove application of the uptake increasing technique by the uptake increasing application device 220 (e.g., lowering a setting of a heating pad, turning a heating pad off, or the like).

Also, in the illustrated embodiment, the uptake decreasing application device 230 is depicted as being attached to or otherwise associated with the application portion 254, and is configured to decrease radiopharmaceutical uptake (e.g., via reduced blood flow) of the application portion 254. Reduction of blood flow in the application portion 254 in various embodiments provides for proportionally or relatively larger blood flow to the target portion 252 (relative to the application portion 254). Thus, a non-uniform distribution of radiopharmaceutical uptake (with increased uptake by the target portion 252) may be achieved, providing improved efficiency in the use of radiopharmaceutical agent (more radiopharmaceutical to the target portion 252 and less radiopharmaceutical to the application portion 254). For example, the uptake decreasing application device 230 may be configured as an icepack or other cooling device and/or a pressurizing device (e.g., pressure sleeve, pressure pants, pressure suit) affixed to, resting on, or otherwise positioned to reduce blood flow of the application portion 254. In the illustrated embodiment, the sensor 232 is also positioned proximate the application portion 254 and is configured to measure a parameter (e.g., temperature, blood flow, pressure, or the like) of the application portion 254. Based on info nation provided by the sensor 232, the control of the uptake decreasing device 230 may be altered. For example, if the value of the measured parameter meets or exceeds a desired value, the application control module 214 may, responsive to receipt of the information from the sensor 232 indicating that the desired value has been met, autonomously reduce or remove application of the uptake decreasing technique by the uptake decreasing application device 230 (e.g., lowering a setting of a pressure device, turning a pressure device off, or the like). In some embodiments, the uptake decreasing application device 230 may be worn, such as a pressure suit or pressure pants.

The depicted administration module 240 is configured to, responsive to the control of the application control module 214, administer a radiopharmaceutical for use with NM imaging. For example, after a predetermined amount of time of application of one more uptake increasing techniques, and/or upon a measured parameter reaching a predetermined level, the application control module 214 may automatically or autonomously control the administration module 240 to administer the radiopharmaceutical. In some embodiments, the administration module 240 may include a pump or other device configured to deliver the radiopharmaceutical via an IV line that has been inserted into the patient. In other embodiments, the administration module 240 may include a syringe operated by a practitioner, for example, responsive to a message or prompt provided from the application control module 214 via the display module 212 instructing the practitioner to administer the radiopharmaceutical.

Thus, as disclosed herein, non-uniform distribution or uptake of radiopharmaceutical may be employed to provide proportionally or relatively greater uptake by a portion of the body to be scanned than uptake by one or more portions not to be scanned. By providing increased uptake by a portion to be scanned relative to one or more other portions, improved image quality and/or reduced radiation dose may be achieved in various embodiments. Further, additionally or alternatively, by increasing the amount of uptake by a portion to be scanned, less expensive imaging equipment or techniques (e.g., lower sensitivity detectors) may be employed.

Figure 5:
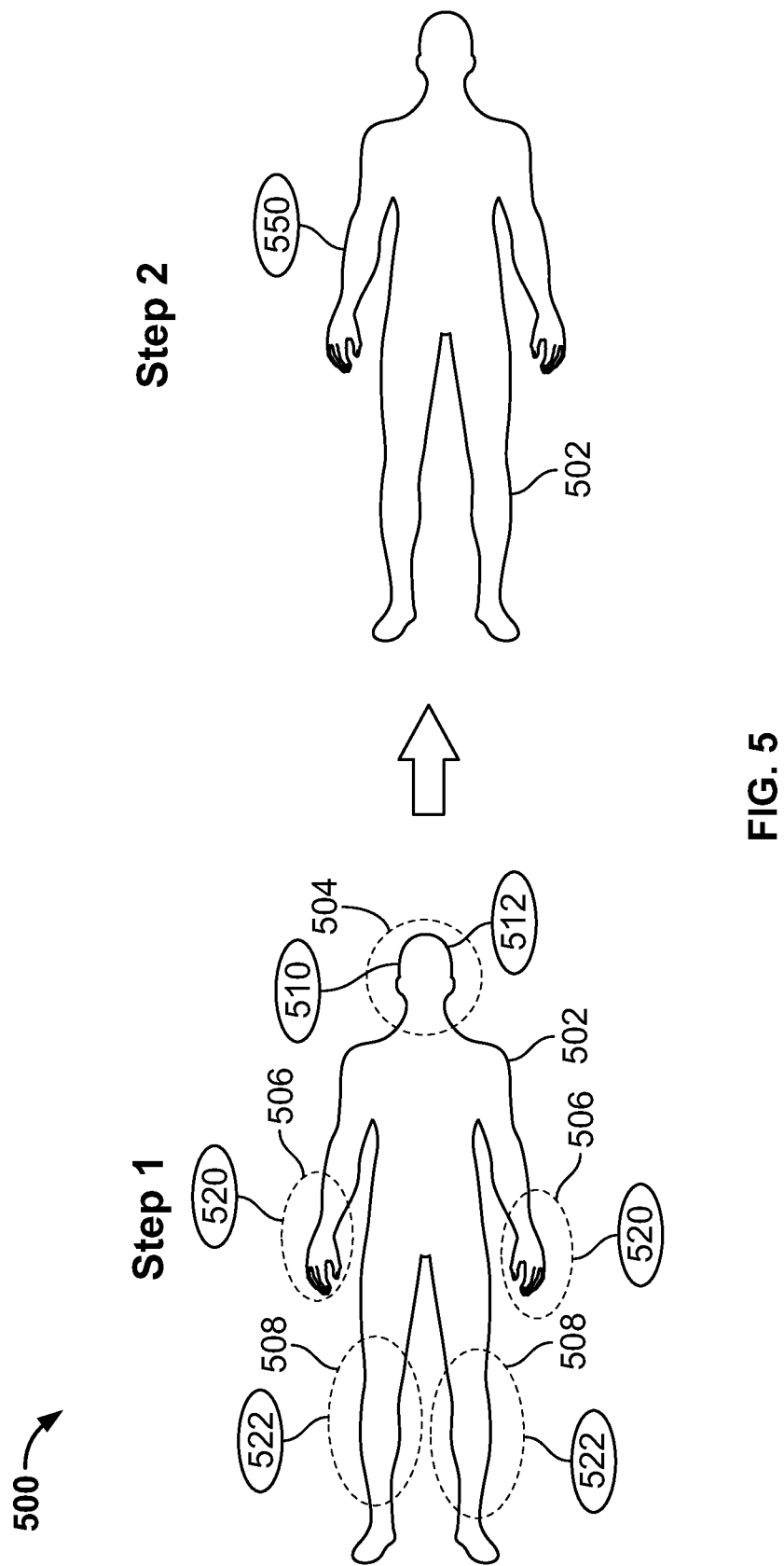
FIG. 5 is a schematic illustration of an example scenario of application of uptake increasing techniques in accordance with various embodiments.

An example scenario 500 of application of uptake increasing techniques in accordance with various embodiments is depicted in FIG. 5. In FIG. 5, a scan is to be performed on a patient 502. The scan, for example, may be a PET scan or SPECT scan that includes the administration of a radiopharmaceutical before acquiring imaging information. In the example scenario 500, a brain scan of the patient 502 is to be performed. For the brain scan, a target portion 504 including the head of the patient 502 is identified. Additionally first application portions 506 (corresponding to the arms) and second application portions 508 (corresponding to the legs) of the patient 502 are identified. Generally, in the example scenario 500, techniques will be employed to increase blood flow to the target portion 504 and to decrease blood flow to the first application portions 506 and second application portions 508, thereby increasing radiopharmaceutical uptake by the target portion 504 relative to other portions of the patient 502, including the first application portions 506 and the second application portions 508, and more efficiently distributing radiopharmaceutical through the body of the patient 502 for the scan.

In the illustrated scenario, a first blood flow increasing technique 510 and a second blood flow increasing technique 512 are applied to the target portion 502. For example, the first blood flow increasing technique 510 may include massaging all or a portion of the bead (e.g., the scalp), while the second blood flow increasing technique 512 may include the application of heat (e.g., via a heating pad placed on the head). Also, in the illustrated scenario, a first blood flow decreasing technique 520 is applied to the first application portion 506, and a second blood flow decreasing technique 522 is applied to the second application portion 508. For example, the first blood flow decreasing technique 520 may include cooling of the first application portions 506 (e.g., via the application of an ice pack), and the second blood flow decreasing technique 522 may include the application of pressure to the second application portions 508 (e.g., via pressurized pants). Thus the blood flow of the target portion 504 relative to the rest of the body of the patient 502 may be increased by increasing blood flow to the target portion 504 and/or decreasing blood flow to one or more other portions of the body. By thus increasing relative blood flow to the target portion 504, the target portion 504 may uptake a relatively higher proportion of radiopharmaceutical delivered via the blood stream.

In the illustrated embodiment, after the uptake increasing techniques (e.g., techniques configured to increase the relative uptake by the target portion 504, by increasing blood flow to the target portion 504 and/or decreasing blood flow to one or more other portions) have been performed for a sufficient amount of time to achieve an appreciable or desired difference in the blood flow to the target portion 504 relative to other portions of the body, a radiopharmaceutical is administered in step two at 550. In the illustrated embodiment, step two or the administration of the radiopharmaceutical is depicted as occurring after step one or the application of uptake increasing techniques; however, it should be noted that the administration of uptake increasing techniques in various embodiments may occur before administration of the radiopharmaceutical, during administration of the radiopharmaceutical, or after administration of the radiopharmaceutical. For example, the illustrated step 1 may be initiated and performed until a desired blood flow distribution is achieved for efficient uptake distribution, then the radiopharmaceutical administered with the uptake techniques still being applied, and, after administration (e.g., injection) of the radiopharmaceutical, the uptake increasing techniques may continue to be applied for an amount of time corresponding to a time for uptake of the radiopharmaceutical in the body from the blood stream. Once most or all uptake is complete, application of the uptake increasing techniques may be ceased. It should also be noted that the particular example scenario 500 is intended by way of example for illustrative purposes. For example, other target portions and/or application portions, and/or additional or alternative uptake increasing techniques may be employed. In various embodiments, one or more uptake increasing techniques may be applied manually. Alternatively or additionally, one or more uptake increasing techniques may be applied autonomously and/or under the control or guidance of one or more processing units.

Figure 3:
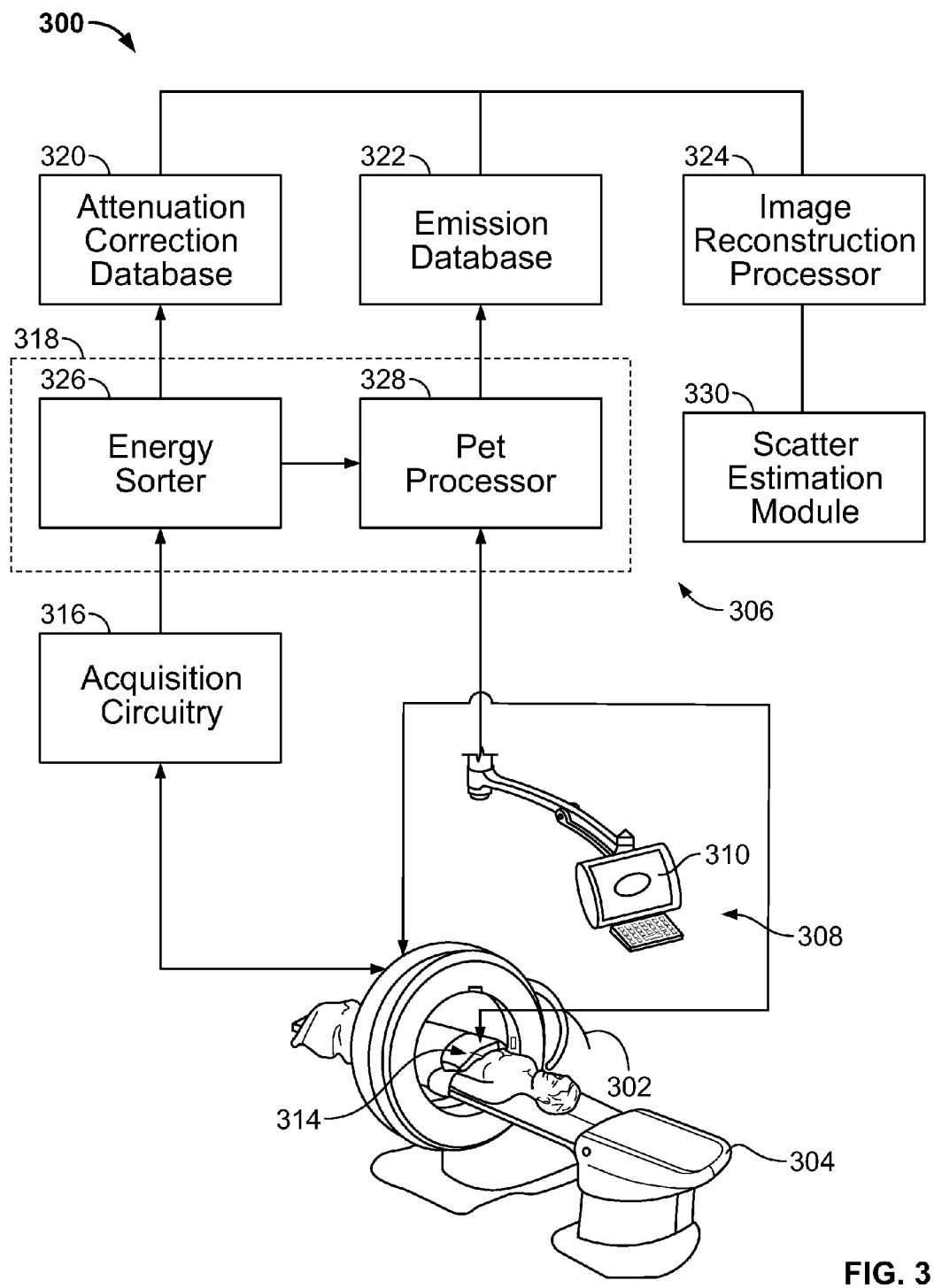
FIG. 3 is a schematic illustration of an exemplary PET medical imaging system in accordance with various embodiments.

Various embodiments may be implemented, for example, in conjunction with a medical imaging system 300 illustrated in FIG. 3, which is shown as a PET system that includes MR imaging capabilities, for example, configured as a multi-modality imaging system, such as a PET/MR imaging system. However, it should be appreciated that various embodiments may be implemented in connection with other modalities additionally or alternatively. Moreover, the imaging detectors may be of different types and configurations. For example, the imaging system may be an MBI (Molecular Breast Imaging) system. It should be noted that an MBI system may be used for screening for breast cancer in non-symptomatic women, for example in women having dense breasts or breast implants. In screening imaging, reducing the exposure of the patient to harmful radiation is of high importance as the patient is most likely healthy.

The medical imaging system 300 generally includes a gantry 302, a patient table 304, and a processing and control system 306 including a user input 308 with a display 310. The gantry 302 provides mechanical support for imaging devices such as, for example, detectors, scanners and transmitters that are used for scanning a patient or other object (e.g., a phantom). The gantry 302 houses imaging devices such as, for example, PET detectors or x-ray detectors. It should be noted that the PET portion of the system in one embodiment is a stationary annular detector, namely a ring of detectors.

The imaging devices on the gantry 302 acquire image data by scanning a patient or other object on the patient table 304. Moving the patient table 304 enables the scanning of various portions of the patient or object. The patient table 304 lies along the axis of the gantry 302, which is known as a viewing area along an examination axis and can be moved along this axis. The patient table 304 can be positioned at various axial positions along the axis. In some embodiments, the gantry 302 includes a plurality of PET detectors that are fixed and spaced on gantry 302, which are positioned radially outward from the axis and that may be configured as one or more rings of detectors. In accordance with other embodiments, the gantry 302 includes a plurality of detectors that are rotatable about the axis. For MR imaging, such as to acquire attenuation information, a receive coil 314 may be placed proximal a portion of interest of the patient. The processing and control system 306 controls the positioning of the patient table 304, as well as receiving data acquired during scanning. In various embodiments, the processing and control system 306 controls the medical imaging system 300 to acquire, for example, image information and/or attenuation information of a volume of interest, for example, a patient and as described in more detail herein. For example, annihilation events may be detected as emission data (e.g., emitted from a patient injected with a radionuclide).

Various processors, sorters, and databases are used to acquire and manipulate emission data, which is used in accordance with various embodiments. The processors, sorters and databases of FIG. 3 include acquisition circuitry 316, an acquisition processor 318, an attenuation correction database 320, an emission database 322, and an image reconstruction processor 324. The acquisition processor 318 is programmed to acquire emission data, for example, in a list mode and/or a sinogram mode, and generate an image based on the emission data acquired in the list mode and/or the emission data acquired in the sinogram mode, which is scatter corrected. The medical imaging system 300 may also include other computing components. The attenuation correction database 320 may include attenuation map data derived from, as one example, MR data, or, as another example, CT data.

In some embodiments, an energy sorter 326 provides, for example, time, location, and energy data to a PET processor 328. The PET processor 328 generally uses the received data to identify pairs of data, also known as coincidence pairs, coincident pair lines and lines of response, corresponding to annihilation events that occurred inside the region of interest. After the acquisition processor 318 identifies an annihilation event, the acquisition processor 318 updates data in the emission data database 322 to store information relating to the annihilation events.

Thus, after an acquisition session has been completed and sets of data have been stored in one or more databases, the image reconstruction processor 324 accesses the data in the databases 320 and 322 and uses the accessed data to generate images that may be requested by a system operator. Additionally, the sets of transmission and emission data are used by a scatter estimation module 330 to perform scatter estimation, particularly multiple scatter estimation (e.g., estimating multiple 3D PET scatter) as described in more detail herein.

Figure 4:
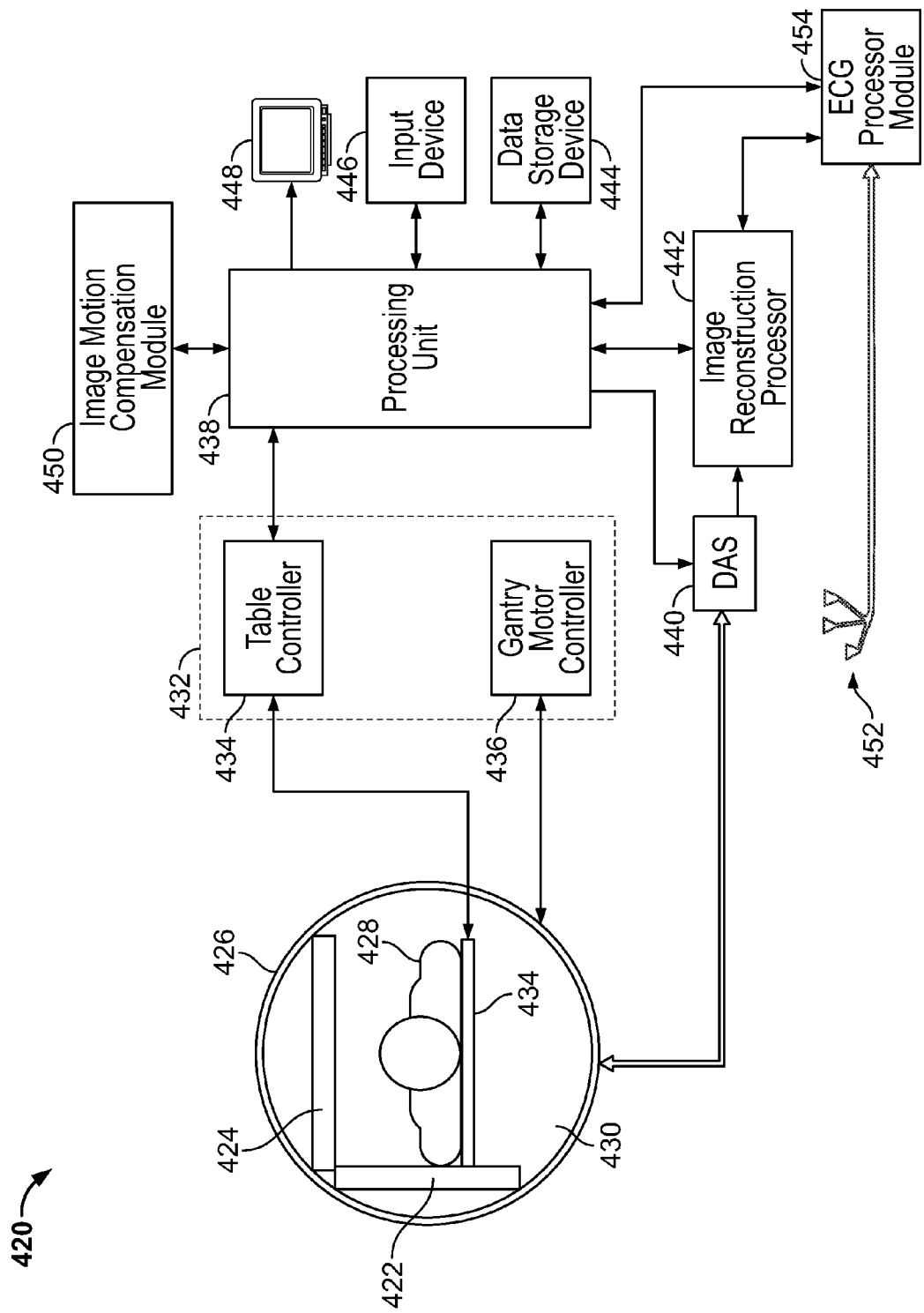
FIG. 4 is a schematic illustration of an exemplary SPECT imaging system in accordance with various embodiments.

Various embodiments may be implemented, for example, in conjunction with a medical imaging system 400 illustrated in FIG. 4, which is shown as a SPECT system. For example, as shown in FIG. 4, the imaging system 420 may generally include a plurality of imaging detectors 422 and 424 (two are illustrated) mounted on a gantry 426. It should be noted that additional imaging detectors may be provided. The imaging detectors 422 and 424 are located at multiple positions (e.g., in an L-mode configuration) with respect to a patient 428 in a bore 430 of the gantry 426. The patient 428 is supported on a patient table 434 such that radiation or imaging data specific to a structure of interest (e.g., the heart) within the patient 428 may be acquired. It should be noted that although the imaging detectors 422 and 424 are configured for movable operation along (or about) the gantry 426, in some imaging systems, imaging detectors are fixedly coupled to the gantry 426 and in a stationary position, for example, in a PET imaging system (e.g., a ring of imaging detectors). It also should be noted that the imaging detectors 422 and 424 may be formed from different materials and provided in different configurations known in the art.

One or more collimators may be provided in front of one or more of the imaging detectors 422 and 424. The imaging detectors 422 and 424 acquire a 2D image that may be defined by the x and y location of the pixel and the location of the imaging detectors 422 and 424. Each of the imaging detectors 422 and 424 has a radiation detection face (not shown) that is directed towards, for example, the patient 428, which may be a human patient or animal. It should be noted that the gantry 426 may be configured in different shapes, for example, as a "C", "H" or "L".

A controller unit 432 may control the movement and positioning of the patient table 434 with respect to the imaging detectors 422 and 424 and the movement and positioning of the imaging detectors 422 and 424 with respect to the patient 428 to position the desired anatomy of the patient 428 within the FOVs of the imaging detectors 422 and 424, which may be performed prior to acquiring an image of the anatomy of interest. The controller unit 432 may have a table controller 434 and a gantry motor controller 436 that each may be automatically commanded by a processing unit 438, manually controlled by an operator, or a combination thereof. The table controller 434 may move the patient table 434 to position the patient 428 relative to the FOV of the imaging detectors 422 and 424. Additionally, or optionally, the imaging detectors 422 and 424 maybe be moved, positioned or oriented relative to the patient 428 or rotated about the patient 428 under the control of the gantry motor controller 436.

The imaging data may be combined and reconstructed into an image compensated composite image as described herein, which may comprise two-dimensional (2D) images, a three-dimensional (3D) volume or a 3D volume over time (4D).

A Data Acquisition System (DAS) 440 receives analog and/or digital electrical signal data produced by the imaging detectors 422 and 424 and decodes the data for subsequent processing as described in more detail herein. An image reconstruction processor 142 receives the data from the DAS 140 and reconstructs an image using any reconstruction process known in the art. A data storage device 144 may be provided to store data from the DAS 140 or reconstructed image data. An input device 146 also may be provided to receive user inputs and a display 148 may be provided to display reconstructed images.

Additionally, ECG leads 452 (or other cardiac activity sensors) are joined to the patient 428 to detect cardiac activity. The leads 428 generate ECG signals that are digitized, processed, filtered and the like, by an ECG processor module 454, which allows, for example, the acquisition of gated cardiac NM data. The ECG processor module 454 may provide the ECG signals to the processing unit 438 and/or to the image reconstruction processor 442. Alternatively, the ECG processor module 442 may process the ECG signals and output to the processing unit 438 and/or to the image reconstruction processor 442 time stamps associated with particular points in the cardiac cycle. The processing unit 438 and/or the image reconstruction processor 442 associates the time stamps or ECG signals with corresponding projection data sets to identify the cardiac activity at the time at which an associated projection data set is obtain. Alternatively, one of the processing unit 438 and/or to the image reconstruction processor 442 may generate, based on the ECG signal, a time stamp.

The time stamps identify a unique point in the cardiac cycle (e.g. the R-wave, the P-wave, X milliseconds following the R-wave and the like). The processing unit 438 and/or to the image reconstruction processor 442 stores the time stamp with, or uniquely correlates the time stamp to, a corresponding projection data set. Thus, each projection data set is associated with a particular table position and gantry rotation angle, as well as a particular point in the cardiac cycle, at which the projection data set was acquired. Each time stamp and corresponding projection data set may be stored in the data storage device 444. The data storage device 444 may store a group of projection data sets for a complete scan or examination of the patient 428 or a region or organ or interest of the patient 428. The group of projection data sets corresponds to a volumetric area of the patient 428.

In operation, in various embodiments, when a photon having energy typical of the energies of photons used in SPECT applications is incident on the imaging detectors 422 and 424, the radiation is detected and recorded as a count once validated using known validation methods. This information is then used to reconstruct an image, for example, using the image reconstruction processor 442, and which may be gated NM images. Moreover, an image motion compensation module 450 may be provided to correct or compensate for motion of an imaged object, which may result in image blurring, and that may be caused, for example, in cardiac imaging from heart motion. The image motion compensation module 450 reduces or compensates for image blurring caused by motion. The image motion compensation module 450 may be a separate module or may be provided as part of the processing unit 438. The image motion compensation module 450 may be implemented in hardware, software, or a combination thereof.

It should be noted that the reconstruction of the emission data may be performed in any suitable manner using any type of image reconstruction process, such as analytical image reconstruction algorithms known in the art. In one embodiment, the images are reconstructed from the scan of the patient or object correcting for multiple scatters using a convolution method having a kernel with an amplitude and width that varies as a function of a filtered attenuation sinogram.

It should be noted that the particular arrangement of components (e.g., the number, types, placement, or the like) of the illustrated embodiments may be modified in various alternate embodiments. In various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), a given module or unit may be added, or a given module or unit may be omitted.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and the like. The storage device may also be other similar means for loading computer programs or other instructions into the computer or processor.

As used herein, the term "computer," "controller," and "module" may each include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the tem "module" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A system comprising:
    a determination module configured to identify a target portion of a patient corresponding to a portion of interest of the patient to be scanned with a nuclear medicine scanning technique; and
    an application control module configured to, based on an identification of the target portion by the determination module, control application of an uptake increasing technique, the uptake increasing technique configured to provide non-uniform radiopharmaceutical distribution to increase uptake of an imaging radiopharmaceutical to the target portion of the patient relative to other portions of the patient other than the target portion, wherein the application control module is configured to control application of the uptake increasing technique temporally proximate to an administration of the imaging radiopharmaceutical to the patient.

2. The system of claim 1, further comprising a display, wherein the application module is configured to provide instruction to an operator to apply the uptake increasing technique via the display.

3. The system of claim 1, wherein the application module is configured to autonomously control an application device configured to apply the uptake increasing technique to a patient.

4. The system of claim 1, wherein the uptake increasing technique comprises a technique that increases blood flow to the target portion relative to the portions of the patient other than the target portion, wherein the system comprises a heating pad configured to be positioned to deliver heat to the target portion to increase blood flow to the target portion relative to the other portions.

5. The system of claim 1, wherein the uptake increasing technique comprises a hydraulic technique that decreases blood flow to at least one of the other portions of the patient other than the target portion relative to the target portion, wherein the system comprises at least one of a tourniquet, pressure sleeve, or pressure pants configured to be applied to the at least one of the other portions of the patient.

6. The system of claim 1, wherein the determination module is configured to receive information corresponding to a scan of the patient to be performed, and wherein the determination module is configured to identify the target portion using the information corresponding to the scan.

7. The system of claim 1, wherein the application control module is configured to control the application of the uptake increasing technique based on information obtained via a sensor configured to sense one or more parameters of the patient.

8. The system of claim 1, wherein the application control module is configured to control administration the imaging radiopharmaceutical based on information obtained via a sensor configured to sense one or more parameters of the patient.

9. A tangible and non-transitory computer readable medium comprising one or more computer software modules configured to direct one or more processors to:
    identify a target portion of a patient corresponding to a portion of interest of the patient to be scanned with a nuclear medicine scanning technique; and
    control application of an uptake increasing technique to at least one of the target portion or an application portion of the patient other than the target portion, the uptake increasing technique configured to provide non-uniform radiopharmaceutical distribution to increase uptake of an imaging radiopharmaceutical to the target portion of the patient relative to other portions of the patient other than the target portion, wherein the uptake increasing technique is applied temporally proximate to an administration of the imaging radiopharmaceutical to the patient.

10. The tangible and non-transitory computer readable medium of claim 9, wherein the computer readable medium is further configured to direct the one or more processors to obtain sensor information from a sensor configured to sense one or more parameters of the patient, and to control an application device to provide the uptake increasing technique base on the sensor information.

11. The tangible and non-transitory computer readable medium of claim 9, wherein the computer readable medium is further configured to control administration of the radiopharmaceutical to the patient.

12. The tangible and non-transitory computer readable medium of claim 9, wherein the uptake increasing technique comprises a technique that increases blood flow to the target portion relative to the portions of the patient other than the target portion.

13. The tangible and non-transitory computer readable medium of claim 9, wherein the uptake increasing technique comprises a technique that decreases blood flow to the at least one of the portions of the patient other than the target portion relative to the target portion.

14. A method for causing non-uniform radiopharmaceutical uptake comprising:
    identifying, with a determination module, a target portion of a patient corresponding to a portion of interest of the patient to be scanned with a nuclear medicine scanning technique;
    applying, with an application control module, an uptake increasing technique to at least one of the target portion or an application portion of the patient other than the target portion, the uptake increasing technique configured to provide non-uniform radiopharmaceutical distribution to increase uptake of an imaging radiopharmaceutical to the target portion of the patient relative to other portions of the patient other than the target portion; and
    administering the imaging radiopharmaceutical to the patient temporally proximate to applying the uptake increasing technique.

15. The method of claim 14, wherein applying the uptake increasing technique comprises applying, with the application control module, a technique that increases blood flow to the target portion relative to the other portions of the patient other than the target portion.

16. The method of claim 15, wherein applying the uptake increasing technique comprises applying heat with a heating pad to the target portion.

17. The method of claim 15, wherein applying the uptake increasing technique comprises massaging the target portion with a mechanical massaging device.

18. The method of claim 14, wherein applying the uptake increasing technique comprises applying a technique that decreases blood flow to the portions of the patient other than the target portion relative to the target portion.

19. The method of claim 18, wherein applying the uptake increasing technique comprises cooling the application portion of the patient other than the target portion.

20. The method of claim 18, wherein applying the uptake increasing technique comprises constricting blood flow with at least one of a tourniquet, pressure sleeve, or pressure pants to the application portion of the patient other than the target portion.

* * * * *